United States Patent
Matsumoto (10) Patent No.: US 7,014,736 B2
(45) Date of Patent: Mar. 21, 2006

(54) APPARATUS AND PROCESS FOR PURIFICATION OF ACRYLIC ACID FAMILY

(75) Inventor: Yukihiro Matsumoto, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/784,553

(22) Filed: Feb. 23, 2004

(65) Prior Publication Data
US 2004/0182693 A1 Sep. 23, 2004

(30) Foreign Application Priority Data
Mar. 18, 2003 (JP) ............................. 2003-074304

(51) Int. Cl.
B01D 3/00 (2006.01)
C07C 69/54 (2006.01)
C07C 51/44 (2006.01)
C07C 67/54 (2006.01)

(52) U.S. Cl. .............................. 203/8; 203/87; 203/98; 203/DIG. 9; 203/DIG. 21; 560/218; 562/600

(58) Field of Classification Search .................... 203/2, 203/87, 98, 8, DIG. 9, DIG. 21; 562/600; 560/218
See application file for complete search history.

(56) References Cited

U.S. PATENT DOCUMENTS

| | | | |
|---|---|---|---|
| 3,803,002 A * | 4/1974 | Skraba et al. ................... 203/1 |
| 4,019,964 A | 4/1977 | Fickel | |
| 4,056,444 A | 11/1977 | Weicht et al. | |
| 4,110,370 A * | 8/1978 | Engelbach et al. .......... 562/600 |
| 4,189,616 A * | 2/1980 | Liebert ....................... 585/701 |
| 4,372,822 A | 2/1983 | Muller et al. | |
| 4,469,558 A | 9/1984 | Watson | |
| 4,471,619 A * | 9/1984 | Nolley, Jr. .................... 60/648 |
| 4,559,108 A | 12/1985 | Ahlberg | |
| 5,876,570 A | 3/1999 | Thigpen | |
| 6,550,274 B1 * | 4/2003 | Agrawal ....................... 62/617 |
| 6,596,129 B1 * | 7/2003 | Yoneda et al. .................. 203/2 |
| 6,632,329 B1 | 10/2003 | Mizutani et al. | |
| 6,641,700 B1 | 11/2003 | Matsumoto et al. | |
| 6,666,956 B1 * | 12/2003 | Nishimura et al. ............ 203/1 |

FOREIGN PATENT DOCUMENTS

| | | |
|---|---|---|
| DE | 1 208 291 | 1/1966 |
| DE | 196 31 332 A1 | 11/1997 |

(Continued)

Primary Examiner—Virginia Manoharan (57) ABSTRACT

An apparatus and a process for purification of an acrylic acid family. The apparatus is an apparatus for distillation purification of the acrylic acid family encompassing acrylic acid and its esters, and includes: a distillation column 10 to which a liquid containing the acrylic acid family is supplied, and from the column top of which a vapor is retrieved, and from the column bottom of which a liquid is retrieved; a condenser 20 which is connected to the column top side of the distillation column 10, and to which the vapor having been retrieved from the distillation column is supplied, and which condenses the supplied vapor and then refluxes a portion of the resultant condensate to the distillation column 10, and from which the residual condensate is retrieved; and a reboiler 30 which is connected to the column bottom side of the distillation column 10, and to which the liquid in the distillation column 10 is supplied, and which heat-boils the supplied liquid and then returns it to the distillation column 10; wherein the reboiler 30 is set in a number of at least two in parallel to the distillation column 10. The process uses the above apparatus.

7 Claims, 4 Drawing Sheets

FOREIGN PATENT DOCUMENTS

| | | |
|---|---|---|
| EP | 1 043 050 A2 | 10/2000 |
| EP | 1 097 742 A1 | 5/2001 |
| GB | 900457 | 7/1962 |
| GB | 1 452 377 | 10/1976 |
| JP | 2000-254403 A | 9/2000 |
| JP | 2000-290226 A | 10/2000 |
| JP | 2001-131116 A | 5/2001 |
| JP | 2001-190901 A | 7/2001 |
| WO | WO 90/07367 A1 | 7/1990 |
| WO | WO 97/44298 A1 | 11/1997 |

* cited by examiner

APPARATUS AND PROCESS FOR
PURIFICATION OF ACRYLIC ACID FAMILY

BACKGROUND OF THE INVENTION

A. Technical Field

The present invention relates to an apparatus and a process for purification of an acrylic acid family. In detail, the subjects of the present invention are: a purification apparatus for obtaining an impurity-removed purified material of high purity in processes for production of acrylic acid and acrylic esters which are used as starting materials for production of various chemical products; and a process for purification of the acrylic acid family with such a purification apparatus.

B. Background Art

Acrylic acid and acrylic esters (which are hereinafter generically referred to as acrylic acid family) are widely used as starting materials for production of various chemical products.

In industrial production of the acrylic acid family, the produced acrylic acid family is purified so as to be appropriate for use purposes and demanded quality of the acrylic acid family. In production of the acrylic acid family, there is a possibility that by-products such as (e.g. maleic acid) (which are formed from propylene used as a starting material) and dimer acid (which is formed in the production process) may be contained as impurities in the produced acrylic acid family. Therefore, a purification step for removing these impurities is needed.

A distillation art is applied to the purification of the acrylic acid family. The purification by the distillation is, for example, carried out as follows: a liquid containing the acrylic acid family is vaporized, and then the resultant vapor containing the acrylic acid family in an increased high proportion and the impurities in a reduced low proportion is retrieved and then condensed, thus purifying the acrylic acid family. As the case may be, the impurities are obtained on the vapor side, and the objective product is obtained on the liquid side.

Various arts are proposed for the purpose of increasing the purification efficiency to thus produce an acrylic acid family of high quality or enhance the productivity.

In particular, because the acrylic acid family is an easily polymerizable substance, there is a problem that its polymer is formed in a purification apparatus to thus adhere to an inner wall surface of the apparatus or clog up the piping. Many arts for solving this problem are proposed.

For example, there is an art in which at least two condensers are set in series with a distillation column, thereby preventing a polymer from forming in the apparatus downstream of the condensers to thus adhere to the apparatus (refer to patent document 1 below).

There is an art in which a vapor-dispersing apparatus is set at a place of connection of a reboiler to a distillation column, thereby preventing the channeling of a vapor in the distillation column to thus prevent a polymer from forming in the distillation column to thus adhere to it, wherein the reboiler heat-reboils a liquid from the distillation column and then circulates it (refer to patent document 2 below).

[Patent Document 1]
  JP-A-131116/2001 (Kokai)
[Patent Document 2]
  JP-A-254403/2000 (Kokai)

In the case where the purification apparatus is large-sized in order to enhance the productivity of the acrylic acid family, there greatly occurs the formation and adhesion of its polymer in the apparatus and, in a bad case, the internal piping of the apparatus may be clogged up with the polymer. Therefore, the operation of the apparatus needs to often be stopped for the work of removing the adhered polymer, so that the production efficiency is deteriorated.

In particular, as to a reboiler having a structure such that many tubes are disposed, a polymer adheres to inner surfaces of the tubes to thus easily cause their clogging and, even if the clogging is not caused, there are disadvantages in that the heat-exchange efficiency is greatly deteriorated, thus resulting in great deterioration of the performance of the entire distillation apparatus.

As to the aforementioned prior arts as described in the patent documents 1 and 2, it is impossible to sufficiently prevent the formation and adhesion of the polymer. Particularly as to the large-sized purification apparatus, even the comparatively-short-term operation undergoes the performance deterioration due to the adhesion of the polymer, and therefore the operation needs to be stopped to carry out the work of removing the polymer.

SUMMARY OF THE INVENTION

A. Object of the Invention

An object of the present invention is to solve the aforementioned problems in the purification of the acrylic acid family by preventing the adhesion of its polymer into purification apparatuses to thus enhance the productivity in the step for purification of the acrylic acid family.

B. Disclosure of the Invention

An apparatus according to the present invention for purification of an acrylic acid family is an apparatus for distillation purification of the acrylic acid family encompassing acrylic acid and its esters and comprises: a distillation column to which a liquid containing the acrylic acid family is supplied, and from the column top of which a vapor is retrieved, and from the column bottom of which a liquid is retrieved; a condenser which is connected to the column top side of the distillation column, and to which the vapor having been retrieved from the distillation column is supplied, and which condenses the supplied vapor and then refluxes a portion of the resultant condensate to the distillation column, and from which the residual condensate is retrieved; and a reboiler which is connected to the column bottom side of the distillation column, and to which the liquid in the distillation column is supplied, and which heat-boils the supplied liquid and then returns it to the distillation column; wherein the reboiler is set in a number of at least two in parallel to the distillation column.

A process according to the present invention for purification of an acrylic acid family is a process for distillation purification of the acrylic acid family with the above apparatus according to the present invention for the purification, and comprises the steps of supplying the liquid from the distillation column to the at least two reboilers and returning the heat-boiled vapor from the reboilers to the distillation column.

These and other objects and the advantages of the present invention will be more fully apparent from the following detailed disclosure.

EXPLANATION OF THE SYMBOLS

10: Distillation column
12: Feed pipe
14: Condensate-retrieving pipe
16: Outlet pipe
20: Condenser
22: Vapor-retrieving pipe
24: Liquid-returning pipe
26: Heating-medium pipe
30: Reboiler
32: Liquid-retrieving pipe
34: Vapor-returning pipe
36: Heating-medium pipe
θ: Interposed angle

DETAILED DESCRIPTION OF THE INVENTION

Hereinafter, detailed descriptions are given about the apparatus and process according to the present invention for purification of the acrylic acid family. However, the scope of the present invention is not bound to these descriptions. And illustrations other than the following illustrations can also be carried out in the form of appropriate modifications of the following illustrations within the scope not departing from the spirit of the present invention.

[Purification of Acrylic Acid Family]

In the present invention, the acrylic acid family is a conception encompassing acrylic acid and acrylic esters. Specifically, examples of the acrylic esters include methyl ester, ethyl ester, isopropyl ester, n-butyl ester, 2-ethylhexyl ester, 2-hydroxyethyl ester, hydroxypropyl ester, and dialkylaminoethyl esters.

Conventional arts for production of the acrylic acid family can be applied to basic arts for production of the above acrylic acid family members. Conventional starting materials and reaction conditions will do if they are set in combination with the conventional arts for production of the acrylic acid family so as to be appropriate for use purposes and demanded quality of the acrylic acid family.

The acrylic acid family having been formed by reaction contains impurities such as unreacted starting materials, additives having been added during the reaction, and by-products involved by the reaction. The purification step is carried out with, for example, a stripping column, an azeotropic dehydration column, a low-boiling-material separation column, or a high-boiling-material separation column in order to remove the unfavorable impurities to thus obtain an acrylic acid family having high purity so as to be appropriate for use purposes and demanded quality.

Examples of materials to be removed by the purification step include: water and high-boiling-point inert hydrophobic organic liquids (e.g. diphenyl ether, diphenyl), which are solvents for absorption of reaction gases; and maleic acid, dimer acid, acetic acid, formaldehyde, acrolein, propionic acid, acetone, furfural, benzaldehyde, and protoanemonin, which are impurities. Usually, the impurity content is favorably in the range of 0.01 to 10 weight %. The purity of the acrylic acid family obtained from the purification step is favorably in the range of 99.0 to 99.99 weight %.

The apparatus comprising the distillation column, the condenser, and the reboilers is used as the apparatus for purification of the acrylic acid family.

[Distillation Column]

The distillation column performs the functions of receiving the supply of the liquid containing the acrylic acid family and then discharging the vapor or liquid containing the objective acrylic acid family for retrieval.

Basically, the same apparatuses as distillation columns which are utilized for conventional distillation apparatuses are usable.

Perforated-plate columns and packed columns are known as common distillation columns. The perforated-plate columns are favorable for preventing the formation of the polymer in the distillation columns. Of the perforated-plate columns, those which use a dual-flow sieve tray are preferable.

The temperature inside the distillation column for carrying out the purification of the acrylic acid family is favorably set at not higher than 120° C., more favorably at not higher than 100° C. In the case where the temperature inside the column is too high, the polymer forms to thus cause the increase of the pressure drop and the clogging of the piping. The temperature inside the column can be adjusted by conditions of heating with the reboilers or by a heating apparatus with which the distillation column is equipped. It is desirable that the temperature inside the column should vary as little as possible and should therefore be stable. Specifically, it is favorable that the variation width of the temperature as measured in an identical position in the distillation column is suppressed in the range of 0 to 10° C. Particularly in the case of the azeotropic dehydration column, the composition varies in the column so much that the variation width of the temperature in an identical position tends to be large.

The shape and size of the distillation column differ according to, for example, its inner structure, the treatment method, and the amount of the acrylic acid family to be treated. However, it is usually favorable that the outer shape of the distillation column is cylindrical. In the case where the outer shape of the distillation column is cylindrical, the outer diameter of the distillation column can be set favorably in the range of 0.5 to 6 m, more favorably 2 to 6 m. The height of the distillation column is favorably in the range of 2 to 40 m. The capacity of the distillation column can be set favorably in the range of 0.5 to 1,000 $m^3$.

The distillation column is equipped with a pipe for introduction of the acrylic acid family which is the raw material to be distilled and with a pipeline for circulation of the liquid between the distillation column and the reboilers or condenser. The distillation column and the reboilers are connected to each other through liquid-retrieving pipes for retrieving the liquid from the distillation column and then supplying the retrieved liquid to the reboilers and through vapor-returning pipes for returning the vapor from the reboilers to the distillation column. Outlet pipes for feeding the liquid to outside are connected to the liquid-retrieving pipes. The distillation column and the condenser are connected to each other through a vapor-retrieving pipe for retrieving the vapor from the distillation column and then supplying the retrieved vapor to the condenser and through a liquid-returning pipe for returning the condensate (having been condensed with the condenser) to the distillation column. To the liquid-returning pipe, there is connected a purified-material-retrieving pipe for retrieving the purified material.

It is usual that the piping is connected in a direction vertical to the outer peripheral surface of the distillation column. However, it is also possible that the piping is connected in a direction inclined to the outer peripheral surface of the distillation column. For example, relative to the outer peripheral side of the distillation column, the piping can be connected not only in a direction toward the central axis of the distillation column but also in a direction deviating a little from the central axis of the distillation column. It is also possible to connect the piping not only in a parallel or vertical direction but also in a direction inclined upward or downward.

A liquid or vapor flow, which gets out and in between the piping and the distillation column, varies by adjusting the connection position and direction of the piping to the distillation column, so that the flow in the distillation column can be equalized or the channeling can be prevented.

If necessary, the piping can be equipped with, for example, a pump, a valve (e.g. a pressure regulation valve, a flow rate regulation valve, a check valve, a satety valve, a drain valve), a flow rate meter, or a thermometer.

The distillation column is further equipped with, for example, a measuring instrument or sensor for detecting the internal temperature or pressure of the distillation column. It is also possible that a pressurizing or pressure-reducing apparatus for adjusting the internal pressure of the distillation column is installed into it.

The flow rate of the unpurified acrylic acid family to be supplied to the distillation column can be set favorably in the range of 0.5 to 100 m$^3$/h.

To the distillation column, there can be supplied a polymerization inhibitor in order to inhibit the polymerization of the acrylic acid family. Examples of usable polymerization inhibitors include hydroquinone monomethyl ether (methoquinone), manganese acetate, copper dibutyldithiocarbamate, N-oxyl compounds, hydroquinone, phenothiazine, and other publicly known polymerization inhibitors. These polymerization inhibitors can be supplied from the column top or middle of the distillation column in, for example, the acrylic acid family, an azeotropic solvent, or water. It is also effective in the polymerization inhibition to cause a molecular-oxygen-containing gas (e.g. air, oxygen) to blow in from the column bottom or from a lower portion of each reboiler.

[Reboilers]

Each reboiler is connected to the column bottom side of the distillation column and performs the functions of receiving the supply of the liquid (having been placed in the distillation column) and then heat-boiling the supplied liquid and then returning it to the distillation column.

Basically, the same apparatuses as reboilers which are utilized for conventional distillation apparatuses are usable.

Types such as multitubular type, spiral type, and plate type are known as the reboilers. Any type is usable. The multitubular type is favorable for preventing the formation and adhesion of the polymer in each reboiler. Of the multitubular types, those which have vertical type structures with vaporizing inside tubes are preferable.

Each reboiler is equipped with a tube through which the supplied liquid is caused to flow and with a shell portion in which the tube is placed and through which a heating medium is caused to flow, wherein the heat exchange between the supplied liquid and the heating medium is performed through the tubular wall of the tube.

The size and capacity of each reboiler can be set so as to be appropriate for the ability as demanded to the purification treatment of the acrylic acid family. In the present invention, because at least two reboilers are used, their sizes and capacities will do if they are set so that the total ability of the at least two reboilers can satisfy the treatment performance as demanded to the entirety of the purification apparatus.

The inner diameter of the tube of each reboiler can be set favorably in the range of 10 to 50 mm, more favorably 15 to 35 mm. The length of the tube is favorably in the range of 1 to 7 m, more favorably 2 to 6 m. The number of the tubes to be installed into each reboiler is favorably in the range of 10 to 3,000. The diameter of the shell portion can be set favorably in the range of 0.2 to 4 m, more favorably not larger than 2 m. In the case where the diameter of the shell portion as designed from the reboiling treatment ability is large, the reboiler is divided into at least two so that the shell portion diameter of each of the divided reboilers may not be too large. Thereby the polymerization inhibition in each reboiler can be achieved well.

For example, steam or a phenyl ether type heating medium (which is art organic solvent) is utilized as the heating medium to be introduced into each reboiler. The temperature of the heating medium is favorably in the range of 80 to 250.degree. C. The pressure of the steam can be set favorably at not higher than 0.6 MPaG, more favorably at not higher than 0.4 MPaG.

Each reboiler is equipped with a supply inlet to which the liquid to be treated is supplied and with a returning outlet from which the reboil-treated vapor is fed out. The supply inlet is connected to the liquid-retrieving pipe of the distillation column, and the returning outlet is connected to the vapor-returning pipe which leads to the distillation column.

The flow rate of the liquid to be treated is set favorably in the range of 1 to 3,000 m$^3$/h. As to the circulation of the liquid to be treated or the vapor between each reboiler and the distillation column, both of forced circulation with, for example, a pump and natural circulation due to, for example, the own weight of the liquid to be treated or the rising power of the vapor are possible. Usually, it is favorable to utilize the natural circulation which can reduce the operation energy.

At least two reboilers per one distillation column are set in parallel thereto. What is meant by parallel is that an identical liquid to be treated is supplied in lots to the at least two reboilers and then reboil-treated with each of them. This is a technical conception which is opposite to the disposition of the at least two reboilers in series such that: an identical liquid to be treated is treated with one reboiler, and thereafter the treated liquid is supplied to another reboiler and then further treated therewith.

The at least two reboilers may be different as to, for example, type, size, shape, or treatment ability. However, the combination of reboilers of the same specifications enables efficient treatment, and besides, facilitates the production of the reboilers and their maintenance and care and is practical. The same specifications refer to equipment of which the basic shape and size are the same. Equipment of which the basic specifications are the same, but which has symmetrical structure, is also included substantially in the same specifications.

Each reboiler is disposed on the column bottom side of the distillation column in order to treat the liquid collecting on the column bottom side in the distillation column. The equal or symmetrical disposition of the at least two reboilers in the periphery of the distillation column can make the at least two reboilers efficiently display their abilities, and besides, such a disposition facilitates the maintenance and care of the reboilers. Specifically, because the distillation column extends in a vertical direction, the at least two reboilers can be disposed in such positions as are point-symmetrical as to the center of the distillation column in a horizontal direction crossing the central axis of the distillation column at right angles. If the reboilers are two in number, they can be disposed in positions being at an equal distance from the distillation column on an extended line of a diameter of the distillation column.

The dispositions of the liquid-retrieving pipes and vapor-returning pipes, through which the at least two reboilers and the distillation column are connected to each other, are also, favorably, equal or symmetrical with respect to the distillation column as the center.

Specifically, it is possible that the vapor-returning pipes are equipped separately to the individual reboilers and set so that the positions of the connection of the vapor-returning pipes to the distillation column can have differences of favorably 0 to 1 m in height and interposed angles of favorably 20 to 180°, more favorably not less than 60°, still more favorably not less than 100°, around the center of the distillation column in a horizontal direction. The interposed angle refers to an angle interposed between virtual lines extended from the respective connection positions of two adjacent vapor-returning pipes to the center of the distillation column. The wider the interposed angle is, the more equally the reboiled vapor can be fed from at least two directions into the distillation column and the more the channeling of the liquid to be treated or the vapor inside the distillation column can be prevented. In the case where the number of the reboilers to be set is two, the largest possible interposed angle is favorably 180°. As the number of the reboilers to be set increases, the largest interposed angle becomes smaller. Also as to the difference in height between the connection positions, its smaller value is more effective in the prevention of the channeling of the liquid to be treated or the vapor inside the distillation column.

If the positions where the liquid-retrieving pipes for supplying the liquid (to be treated) from the distillation column to the reboilers are equipped to the distillation column are also set so that the liquid (to be treated) can be retrieved equally from the distillation column, then, for example, the stagnation of the liquid (to be treated) in the distillation column and the bias of the temperature therein can be prevented. Specifically, similarly to the vapor-returning pipes, it is effective to lessen the difference between the height positions or widen the interposed angles or set the liquid-retrieving pipes in equal or symmetrical positions in the outer periphery of the distillation column.

The liquid-retrieving pipes can be set so as to have a branching structure such that one end is connected to the center of the column bottom of the distillation column and that the other end branches off in at least two directions so as to be connected to their respective reboilers. In addition, it is also possible that the at least two reboilers are connected to the column bottom of the distillation column through separate liquid-retrieving pipes. Both in these cases, it is desirable that the conditions such as lengths, curves, and connection height positions of the pipes should be set so as to be the same as those of each other in order that no difference may be made between pressure drops caused when the liquid passes from the column bottom to the reboilers. Such a structure would make it possible to avoid a problem that the retrieving of the liquid (to be treated) from the distillation column has a bias toward a specific reboiler.

Also as to the vapor-returning pipes, similarly to the liquid-retrieving pipes, it is desirable that the conditions of the pipes to be equipped should be set so that the pressure drops caused when the gas passes from the reboilers to the distillation column can be equal. From the viewpoint of the polymerization prevention in the pipes, it is desirable to make the pipes as short as possible. It is favorable to connect the pipes directly at the shortest distances from the reboilers to the distillation column. If the vapor-returning pipes are equipped separately to the individual reboilers, then it is possible to well disperse the gas into the distillation column.

[Condenser]

The condenser is connected to the column top side of the distillation column and performs the functions of receiving the supply of the vapor (having been retrieved from the distillation column) and then condensing the supplied vapor and then refluxes a portion of the resultant condensate to the distillation column and discharging the residual condensate for the retrieve.

Basically, the same apparatuses as condensers which are utilized for conventional distillation apparatuses are usable. The reboilers and the condenser are common to each other in point such that they perform the heat-exchange function. Therefore, as to such as type, structure, size and shape of the condenser, conditions common to the case of the aforementioned reboilers can be adopted.

Also as to the condenser, the multitubular type, particularly, those which have vertical type structures condensed inside tube, can favorably be used.

Per one distillation column, only one condenser may be set or, similarly to the aforementioned reboilers, at least two condensers may be set. Also in this case, it is desirable to dispose the condensers in parallel to the distillation column, and the same disposition conditions as those of the aforementioned reboilers can be adopted.

The heating medium used for the condenser is a low-temperature heating medium or cooling medium for cooling the vapor having been fed from the distillation column. As to the heating medium, the same materials as used for conventional condensers are usable. Specific favorable examples thereof include water and an aqueous ethylene glycol solution. As to the heating medium, heating medium materials having low melting points and low viscosities are favorable. The aqueous ethylene glycol solution favorably has an ethylene glycol concentration of 10 to 50 weight %. The temperature of the heating medium is set favorably in the range of 0 to 50° C.

The size and capacity of the condenser can be set so as to be appropriate for the ability as demanded to the purification treatment of the acrylic acid family. In the case where at least two condensers are used, their sizes and capacities will do if they are set so that the total ability of the at least two condensers can satisfy the treatment performance as demanded to the entirety of the purification apparatus.

In the case where at least two condensers are used, the specifications of, for example, tube and shell portion can be set in almost the same ranges as those of the reboilers. In the case where only one condenser is used, its capacity is set so as to be larger than in the case where at least two condensers are used. Particularly the diameter of the shell portion is favorably set so as not to be larger than 3 m. In the case where the diameter of the shell portion cannot help being too large, the condenser also had better be used in a number of at least two.

To the condenser, there are connected the vapor-retrieving pipe for feeding the vapor from the distillation column and the liquid-returning pipe for feeding the liquid (having been treated by condensation) back to the distillation column. In the case where at least two condensers are used, these condensers may be connected to the distillation column through separate vapor-retrieving pipes or liquid-returning pipes. Or it is also possible that at least two vapor-retrieving pipes or liquid-returning pipes having been connected to the at least two condensers are joined together on the way and then connected to the distillation column.

In the case where the position of the connection of each of the vapor-retrieving pipe and the liquid-returning pipe to the distillation column is separated into at least two, it is favorable, similarly to the case of the reboilers, to lessen the difference between the height positions or widen the interposed angles.

The flow rate of the vapor to be supplied from the distillation column to the condenser can be set favorably in the range of 1 to 100 tons/h. As to the circulation of the vapor or condensate between the condenser and the distillation column, either of the forced circulation and the natural circulation is adoptable.

As to the condensate having been fed out of the condenser, it is possible that a portion thereof is refluxed to the distillation column, and that the rest is retrieved as a purified product of the acrylic acid family. It is also possible that the above rest is fed into an apparatus for an after-step treatment of the acrylic acid family.

[Purification Process]

Basically, techniques common to conventional processes for distillation purification of the acrylic acid family are applicable, except for the use of the purification apparatus according to the present invention.

The reboiler is equipped in a number of at least two. Therefore, when the liquid to be reboil-treated is supplied from the distillation column to the reboilers, the liquid is supplied in lots to the at least two reboilers. Hereupon, it is favorable to equally supply the liquid to the at least two reboilers. Thereby the formation and adhesion of the polymer in the distillation column and the reboilers can be prevented, so that efficient reboiling treatment can be carried out. Particularly, the vapor being returned from the returning pipes of the reboilers to the distillation column can prevent channeling in the distillation column, so that the distillation treatment in the distillation column is well carried out. It is possible to make the at least two reboilers equally display their treatment abilities to thus enhance the total treatment ability, so that efficient reboiling treatment can be carried out.

If the at least two reboilers have the same specifications and are equally or symmetrically disposed in parallel to the distillation column, then the equal supply of the liquid to be treated is easy.

(Effects and Advantages of the Invention)

As to the apparatus and process according to the present invention for purification of the acrylic acid family, the liquid having been placed in the distillation column is reboiled with at least two reboilers which are disposed in parallel to the distillation column. Therefore, the adhesion of the polymer to the inside of the apparatus and the clogging involved by this adhesion can be prevented without spoiling the treatment ability of the reboilers or spoiling the quality performance of the purification operation, when compared with the case where the reboiling treatment is carried out with only one reboiler. It is possible to prevent the channeling of the liquid or vapor in the distillation column to thus stabilize the inside temperature and thereby achieve the stabilization of the distillation purification treatment and the efficiency enhancement of this treatment.

As a result, it is possible to extend intervals between, for example, inspection and cleaning operations of the inside of the apparatus or omit them, and therefore it is possible to carry out a high-quality purification operation durably for a long time, and therefore it is possible to greatly contribute also to the enhancement of the efficiency of the production of the acrylic acid family or to the reduction of costs of the production of the acrylic acid family.

DETAILED DESCRIPTION OF THE PREFERRED EMBODIMENTS

[Structure of Purification Apparatus]

Figure 1:
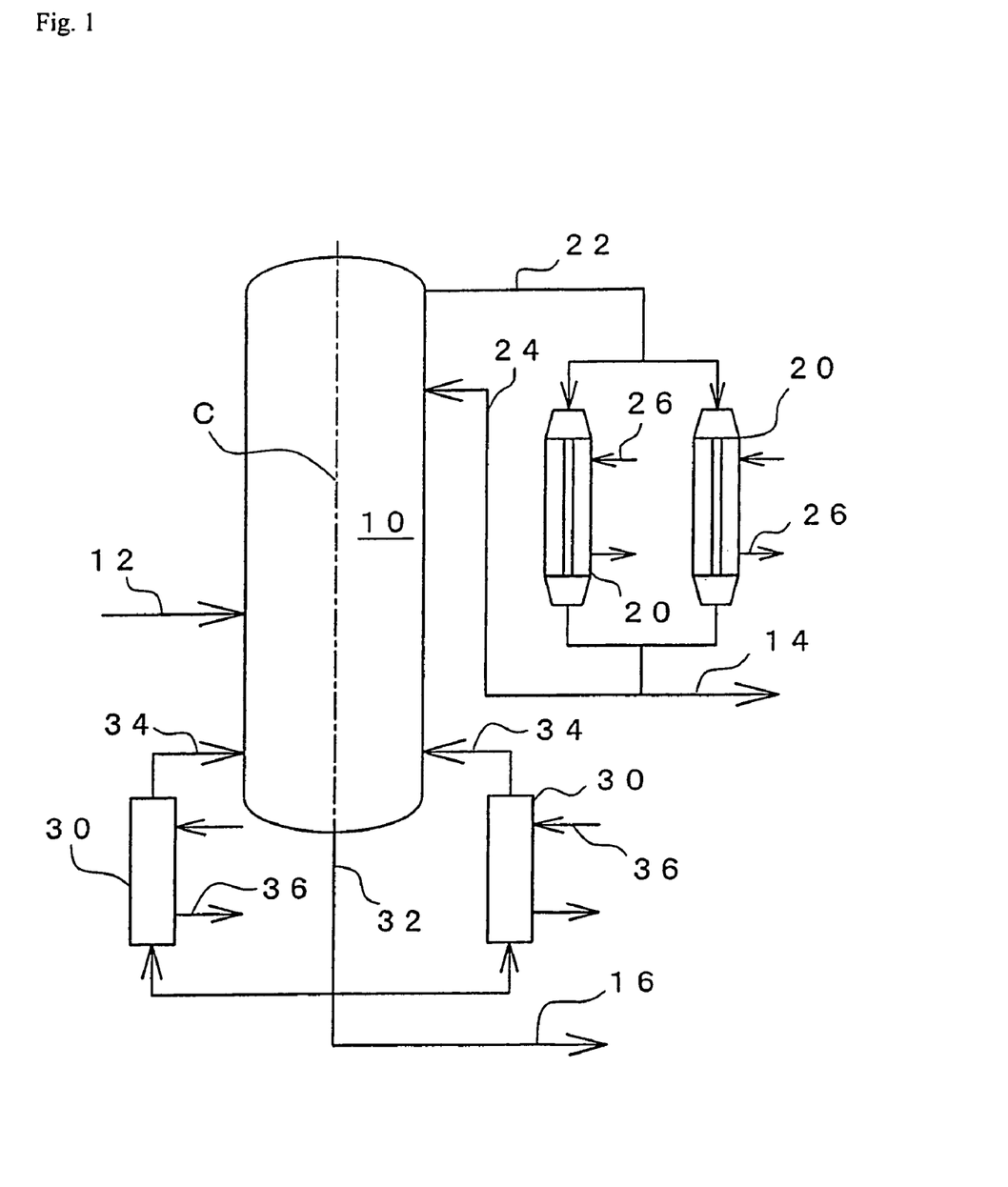
FIG. 1 is a whole structural view of a purification apparatus illustrating a mode for carrying out the present invention.
Figure 2:
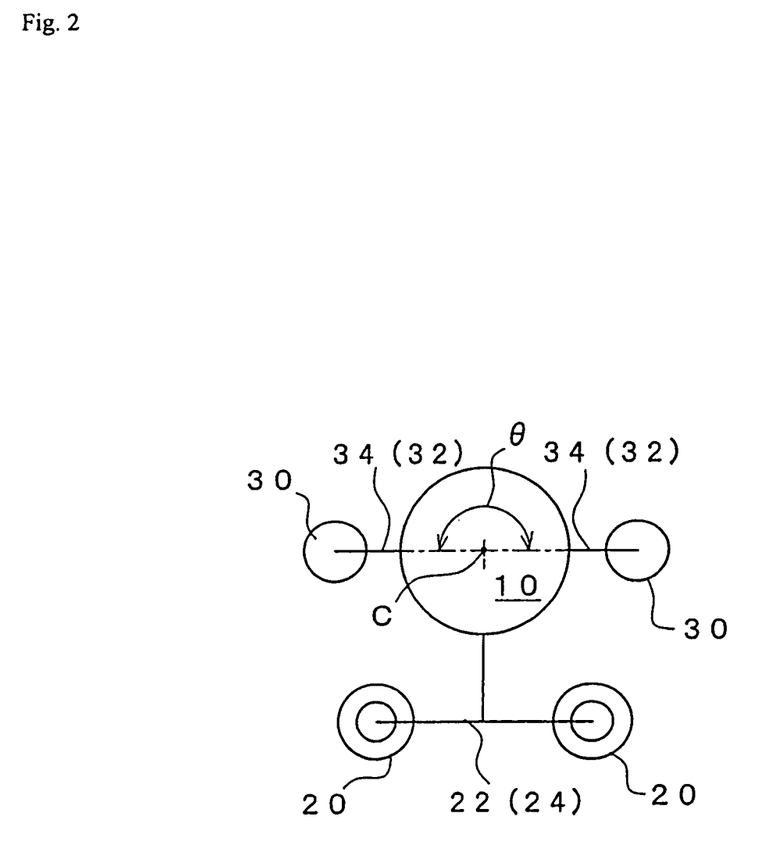
FIG. 2 is a plan view illustrating the disposition structure of the equipment of the purification apparatus of FIG. 1.

The purification apparatus as shown in FIGS. 1 and 2 is equipped with the reboiler and the condenser in a number of two each in parallel to one distillation column.

As is shown in FIG. 1, the distillation column 10 has a column structure having a cylindrical tank which is long in a vertical direction. A pipe 12 for introducing the liquid to be treated is connected to the distillation column 10 on the way of its height direction. A vapor-retrieving pipe 22 for retrieving the vapor having been formed in the distillation column 10 is connected to an upper portion of the distillation column 10. A column-bottom-liquid-retrieving pipe 32 for retrieving the liquid to be treated is connected to the column bottom center of the distillation column 10.

The column-bottom-liquid-retrieving pipe 32 branches off in three directions. One of the branches is an outlet pipe 16 for feeding the liquid to outside. The residual two-direction branches extend symmetrically as to the distillation column 10 and then are connected to separate reboilers 30.

<Reboilers>

The reboilers 30 have a function as heat exchangers for heat-boiling the liquid having been retrieved from the distillation column 10. As the reboilers 30, there are used those of which the entireties are approximately cylindrical and which have a multitubular type vertical structure with vaporizing inside tubes. The reboilers 30 receive the supply of the liquid from their lower end sides and then feed out the boiled liquid, that is, the vapor, from their upper end sides.

To the lower ends of the reboilers 30, there is connected one end each of the column-bottom-liquid-retrieving pipe 32 of the distillation column 10. Another end of the column-bottom-liquid-retrieving pipe 32 is connected to a place where the central axis C of the distillation column 10 penetrates the column bottom, and this pipe extends downward from the above place of the connection to the distillation column 10 and then branches off right and left and then is connected to the right and left reboilers 30. To the branching position of the column-bottom-liquid-retrieving pipe 32, there is connected the outlet pipe 16.

To each of the upper ends of the reboilers 30, there is connected a vapor-returning pipe 34. The other end of the vapor-returning pipe 34 is connected to the outer peripheral side of the distillation column 10. The reboilers 30 are equipped with heating-medium pipes 36, 36 for circulating a heating medium.

As the right and left reboilers 30, the reboilers 30, 30 of the very same specifications are symmetrically disposed. That is to say, they are disposed in parallel in positions of the same height at the same distance from the distillation column 10. In the horizontal shape as shown in FIG. 2, a pair of right and left reboilers 30 are disposed in positions which are symmetrical as to the central axis C of the distillation column 10 in its diameter direction. The vapor-returning pipes 34 having been connected to the upper ends of the reboilers 30 extend toward the central axis C of the distillation column 10 in its radius direction and then are connected to symmetrical positions of the outer peripheral surface of the distillation column 10. The interposed angle θ between the pair of reboilers 30, or between the positions where the vapor-returning pipes 34 are attached to the distillation column 10, around the central axis C is 180°.

<Condensers>

Two condensers 20, 20 are disposed in parallel by the side of the distillation column 10 on its column top side.

Similarly to the reboilers 30, the condensers 20 being used are also those of which the entireties are approximately cylindrical and which have a multitubular type vertical structure condensed inside tube. The condensers 20 receive the supply of the vapor from their upper end sides and then discharge the condensate from their lower end sides. To the lower end of each condenser 20, there is connected a vapor-retrieving pipe 22 which leads to the distillation column 10. The vapor-retrieving pipe 22 branches into two on the side of the connection with the condensers 20, but these two branches are joined together on the way and then connected to the outer peripheral side of the distillation column 10. To the lower ends of the condensers 20, there are connected condensate-returning pipes 24. These condensate-returning pipes 24 are joined together and then connected to the outer peripheral side of the distillation column 10. Downstream of the junction position, the condensate-returning pipe 24 branches from the connection route leading to the distillation column 10 and then is connected to a condensate-retrieving pipe 14 for retrieving the purified liquid. The condensers 20 are further equipped with heating-medium pipes 26, 26 through which a cooling-medium circulates.

As is shown in FIG. 2, the horizontal disposition of the condensers 20 is such that the condensers 20 are disposed in their respective positions which are by the side of the distillation column 10 and line-symmetrical as to a diameter line crossing the central axis C of the distillation column 10. The vapor-retrieving pipes 22 are also similarly line-symmetrically disposed. The right and left vapor-retrieving pipes 22 are joined together and then connected to the distillation column 10 along the axis of symmetry. Though being omitted from the drawings, the same disposition structure as that of the vapor-retrieving pipes 22 is adoptable also for the condensate-returning pipes 24.

[Purification Step]

An unpurified liquid of the acrylic acid family having been produced by another step or with another apparatus is supplied from the feed pipe 12 to the distillation column 10.

The unpurified liquid, having collected in the distillation column 10, refluxes between the column-bottom-liquid-retrieving pipe 32, the pair of reboilers 30, and the vapor-returning pipes 34. By supplying the heating medium to the heating-medium pipes 36, the reboilers 30 heat-boil the refluxing liquid and then feed it back to the distillation column 10.

In the distillation column 10, the vapor of the unpurified liquid rises. Depending on the difference between properties of components as contained in the unpurified liquid, the acrylic acid family as contained in the unpurified liquid rises to the top of the distillation column 10. However, impurities can rise only so far and then fall. In the vapor having risen to the top of the distillation column 10, the purity of the acrylic acid family is high, and the impurity content is low.

The vapor, having been fed out to the vapor-retrieving pipe 22 at the top of the distillation column 10, is condensed in the condensers 20 and then fed out to the liquid-returning pipes 24. The condensate, having been fed out to the liquid-returning pipes 24, is the acrylic acid family having been purified to high purity, and a portion of the condensate is retrieved from the condensate-retrieving pipe 14 and then handled as a product.

The residual condensate is returned to the distillation column 10 and then migrates to the column bottom side of the distillation column 10 to thus return to the liquid (to be treated) having collected on the column bottom side.

The unpurified acrylic acid family having been supplied from the feed pipe 12 can continuously be subjected to the purification treatment and then recovered, by continuously carrying out the reboiling treatment of the liquid (to be treated) (having been in the distillation column 10) with the reboilers 30 and the recovery of the purified acrylic acid family from the condensers 20.

In such a purification treatment, there is a possibility that the polymerization of the acrylic acid family may occur inside such as the distillation column 10, the reboilers 30, the condensers 20, and the pipes 22, 24, 32, 34 connecting them. The polymerization of the acrylic acid family tends to occur in places where there stagnate liquids containing the acrylic acid family and liquids resultant from the condensation of the vapor. If the channeling occurs in a flow of the liquid or vapor, the polymer tends to adhere to the inner wall surface of the apparatus at portions where the flow stagnates. For example, as to the reboilers 30 or condensers 20 in which a plurality of tubes are disposed, if the flow stagnates in part of the tubes, then there may occur problems such that the polymer adheres to the inner wall surfaces of the tubes to thus make the flowing difficult or clog up the tubes. If the channeling occurs to the flow of the liquid or vapor in the distillation column 10, there occurs the adhesion of the polymer to the inner wall surface of the distillation column 10 or to its inner equipment members in places where the flow tends to stagnate, so that the distillation function is hindered.

However, as to the aforementioned mode for carrying out the present invention, the liquid in the distillation column 10 is supplied equally to the two reboilers 30 (which are disposed in structure symmetrical as to the distillation column 10 and in parallel to the distillation column 10) and then reboil-treated therewith. When compared with the case where one large-capacity and large-sized reboiler 30 having the same reboiling ability is used, the formation and adhesion of the polymer are prevented from occurring in the reboilers 30. Its reason is as follows. As the capacity and size of the reboiler 30 becomes larger, there increases a tendency to make differences between the plurality of tubes as to the flow rate and amount of the liquid. For example, it is difficult to avoid making a difference between the central portion and outer peripheral portion of the reboiler 30 as to the flow. Also as to the heating function by the heating medium, there is a possibility that a difference may be made between the central side and the outer peripheral side. If two comparatively small-sized reboilers 30 are made to perform the same treating ability as that of the above one large-sized reboiler 30, then the unevenness and channeling of the flow of the liquid in each reboiler 30 are lessened, so that the possibility of the formation and adhesion of the polymer is reduced.

Similarly also as to the condensers 20, if two comparatively small-sized condensers 20 are made to perform the same treating ability as that of one large-sized condenser 20, then, when compared with this one large-sized condenser 20, the flow of the vapor or condensate in the condensers 20 becomes adequate, so that the possibility of the formation and adhesion of the polymer is reduced.

Because the positions of the connection of the vapor-returning pipes 34 from the two reboilers 30 to the distillation column 10 are disposed symmetrically as to the distillation column 10, the flow of the vapor having been returned to the distillation column 10 is equalized in a horizontal direction of the distillation column 10, so that the local channeling is prevented. Thereby the adhesion and formation of the polymer in the distillation column 10 can also be prevented. The distillation function in the distillation column 10 is also equalized in its entirety, so that the efficient distillation function can be achieved.

[Another Example of Apparatus Structure]

Figure 3:
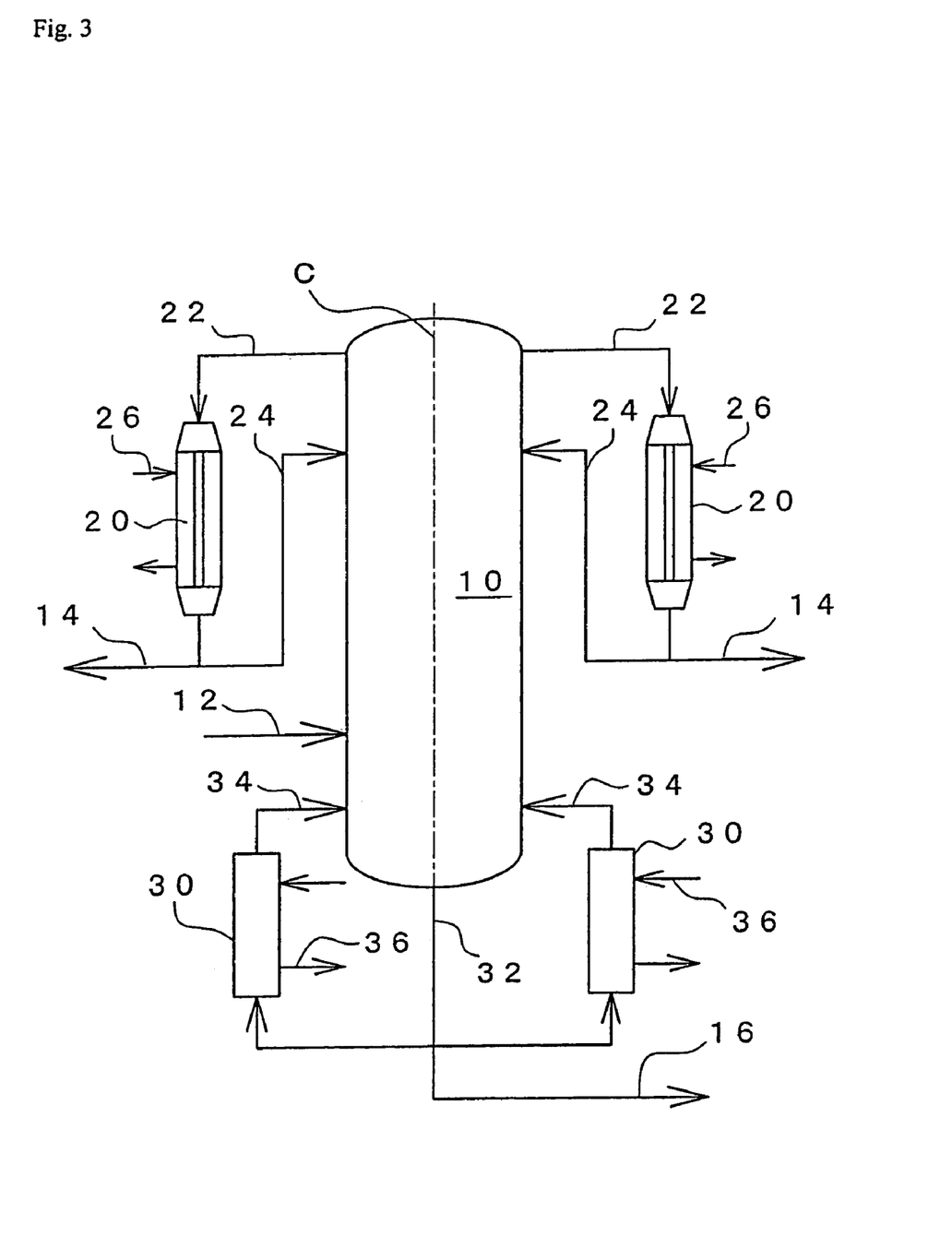
FIG. 3 is a whole structural view of a purification apparatus illustrating another mode for carrying out the present invention.
Figure 4:
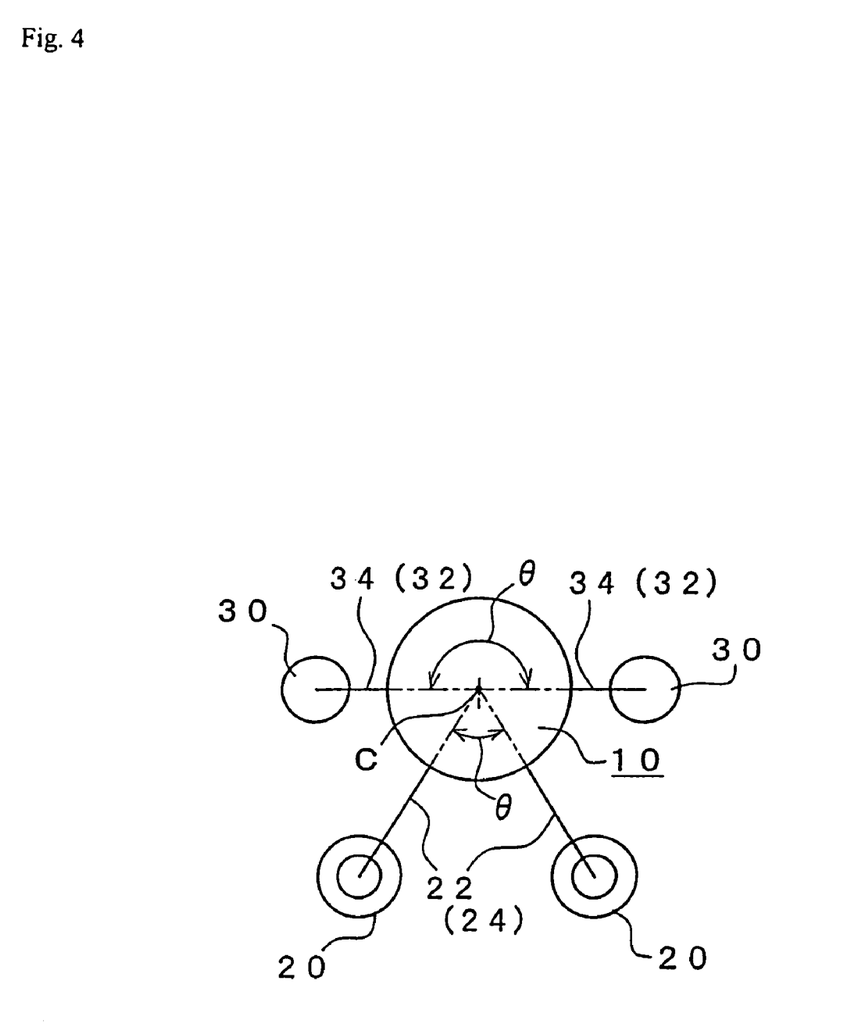
FIG. 4 is a plan view illustrating the disposition structure of the equipment of the purification apparatus of FIG. 3.

The mode for carrying out the present invention, as shown in FIGS. 3 and 4, is common to the aforementioned one as to the basic apparatus constitution, but differs therefrom as to the piping connection structure between the condenses and the distillation column 10.

As is shown in FIG. 3, two condensers 20, 20 are connected to the distillation column 10 through pipelines independent of each other. A vapor-retrieving pipe 22 for supplying the vapor from the distillation column 10 to the condenser 20 and a liquid-returning pipe 24 for returning the condensate from the condenser 20 to the distillation column 10 are equipped to every condenser 20. A liquid-feeding-out pipe 14 is connected to the way of each liquid-returning pipe 24. Incidentally, though being omitted from the drawings, the two liquid-feeding-out pipes 14 may be joined together and then led to the next step.

As is shown in FIG. 4, in the horizontal structure, the two condensers 20, 20 are disposed in positions which are bilaterally symmetrical as to a diameter of the distillation column 10 as the axis of symmetry. The vapor-retrieving pipe 22 and liquid-returning pipe 24 of each condenser 20 extend from a direction along a radius of the distillation column 10 to its center C and then are connected to the distillation column 10 to cross each other at an interposed angle θ. In the drawings, the interposed angle θ is set at a narrow angle of about 60° in order to indicate the condensers together with the reboilers 30. However, it is also possible to set a wider interposed angle θ. For example, it is also possible to set the interposed angle θ between the condensers at the same interposed angle θ=180° as that between the reboilers 30.

WORKING EXAMPLES

Hereinafter, the present invention is more specifically illustrated by the following Examples of some preferred embodiments in comparison with Comparative Examples not according to the present invention. However, the present invention is not limited to them in any way.

Purification apparatuses according to the present invention were specifically constructed to carry out treatment for purification of the acrylic acid family. The results are shown below.

Example 1

Basically, a purification apparatus having the structure shown in FIGS. 3 and 4 was used.
<Distillation Column>
Column diameter=4 m, being equipped with 50 dual-flow sieve trays, material=SUS 316.
<Condensers>
Vertical multitubular type condensers were used. Two condensers were disposed at the interposed angle θ=180°, in other words, on an extended line of a diameter of the distillation column 10, as shown in FIG. 4.
Tubes: outer diameter=38.1 mm, tubular wall thickness=2.11 mm,
length=3,048 mm
number of tubes=1,160, material=SUS 316
Shell portion: outer diameter=1,800 mm
<Reboilers>
Vertical multitubular type reboilers were used. Two reboilers were set in the disposition as shown in FIG. 4.
Tubes: outer diameter=38.1 mm, tubular wall thickness=2.11 mm,
length=4,000 mm
number of tubes=894, material=SUS 316
Shell portion=outer diameter=1,600 mm
Interposed angle between the two reboilers: θ=180°
<Purification Operation>
A liquid containing unpurified acrylic acid (containing acrylic acid 96.5 weight %, acrylic acid dimer 1.9 weight %, maleic acid 0.4 weight %, and phenothiazine 200 weight ppm) was supplied at 18.7 m$^3$/h from the feed pipe 12 to the distillation column 10.

Distillation was carried out under conditions of column top pressure of the distillation column 10=3.3 kPa, reflux ratio=1.5. As a result, a vapor containing acrylic acid 99.9 weight % and maleic acid 40 weight ppm was obtained in the vapor-retrieving pipes 22 at the column top. When compared with the unpurified liquid, the purity of acrylic acid is enhanced, and most of impurities such as the acrylic acid dimer are removed.

The obtained vapor was supplied from the vapor-retrieving pipes 22 (having a pipe diameter of 1,800 mm each) to a pair of condensers 20, 20 and then condensed from 56° C. to 40° C. Cooling water of 30° C. was passed through the heating-medium pipes 26 of the condensers 20. A portion of the condensate having been fed out to the liquid-returning pipes 24 was returned to the distillation column 10, and the residual condensate was retrieved to the condensate-retrieving pipes 14.

On the column bottom side of the distillation column 10, a column bottom liquid was fed from the column-bottom-liquid-retrieving pipe 32 (having a pipe diameter of 1,100 mm) to a pair of reboilers 30, 30 by natural circulation. A portion of the column bottom liquid was extracted from the outlet pipe 16. The liquid was vaporized in the reboilers 30. The resultant vapor was returned from the vapor-returning pipes 34 (having a pipe diameter of 1,250 mm) to the distillation column 10. Saturated steam of 0.6 MPaG was supplied to the heating-medium pipes 36 of the reboilers 30. Molecular oxygen gas was supplied at 20 Nm$^3$/h from lower portions of the reboilers 30. The molecular oxygen gas performs the polymerization inhibition function.

The purification apparatus was operated under the above operational conditions for 1 month. After the end of the operation, the inside of the apparatus was inspected. Almost no polymer was seen inside any of the distillation column 10, the condensers 20, and the reboilers 30.

Comparative Example 1

As to the purification apparatus of Example 1, the condensers 20 and the reboilers 30 were modified as follows.
<Condenser>
Only one condenser of the vertical multitubular type was set.
Tubes: outer diameter=38.1 mm, tubular wall thickness=2.11 mm, length=3,048 mm
number of tubes=2,320, material=SUS 316
Shell portion: outer diameter=2,500 mm When compared with the condensers of Example 1, the number of the tubes per one condenser is larger, and the diameter of the shell portion is also larger. The condensation treatment ability is equal to the total of the two condensers of Example 1.

<Reboiler>

Only one reboiler of the vertical multitubular type was set.
Tubes: outer diameter=38.1 mm, tubular wall thickness=2.11 mm,
length=4,000 mm
number of tubes=1,788, material=SUS 316
Shell portion: outer diameter=2,250 mm When compared with the reboilers of Example 1, the number of the tubes per one reboiler is larger, and the diameter of the shell portion is also larger. The reboiling treatment ability is equal to the total of the two reboilers of Example 1.

<Purification Operation>

The operation was carried out under the same conditions as of Example 1. A vapor containing acrylic acid 99.9 weight % and maleic acid 180 weight ppm was obtained from the column top of the distillation column 10. The resultant purified material itself does not differ from that of Example 1 so much.

However, after the operation for 21 days, the pressure drop in the distillation column 10 increased, and therefore the operation was stopped. On inspection of the inside of the distillation column 10, the condenser 20, and the reboiler 30, it was found that a polymer had accumulated in an amount of 55 kg on the trays, as installed in the distillation column 10, and in an amount of 2 kg on the upper tubular plate inside the condenser 20. As to the reboiler 30, unfavorably, fifty-seven tubes were clogged up with the polymer.

Example 2

A purification apparatus having the structure shown in FIGS. 1 and 2 was used. Basically, the specifications common to those of Example 1 were adopted. However, the structures of the condensers differ therefrom. Only the different items of the specifications are explained below.

<Condensers>

Basically, they are common to those of Example 1. The different items of the specifications are as follows.
Tubes: length=6,096 mm, number of tubes=2,948
Shell portion: outer diameter=2,800 mm As is shown in FIG. 2, the vapor-retrieving pipe 22 and the liquid-returning pipe 24, both of which had a branching structure, were used as the connection structures between the two condensers and the distillation column 10.

<Purification Operation>

An aqueous solution containing unpurified acrylic acid (containing acrylic acid 67.5 weight %, acetic acid 2.2 weight %, water 28.6 weight %, and the balance comprising, for example, maleic acid, acetoaldehyde, and acrolein, and hydroquinone 200 weight ppm) was supplied at 25.0 m³/h from the feed pipe 12 to the 23rd plate of the distillation column 10.

Azeotropic distillation was carried out under a column top pressure of 18.7 kPa of the distillation column 10. The column top liquid, having been retrieved from the vapor-retrieving pipe 22 at the column top and then condense-treated with the condensers 20, separated into two phases. The toluene phase, which was an azeotropic agent, was all refluxed to the distillation column 10. The water phase was distillated as wastewater. The reflux amount was 60 m³/h. Phenothiazine, which was a polymerization inhibitor, was added to the reflux liquid in an amount of 150 weight ppm.

As a result, a purified material comprising acrylic acid 96.2 weight % and acetic acid 300 weight ppm was obtained as the column bottom liquid.

The vapor-retrieving pipe 22, through which the vapor was introduced from the distillation column 10 into the condensers 20, had a pipe diameter of 1,800 mm on the distillation column 10 side and had a pipe diameter of 1,300 mm as those of the branch portions which were connected to the two condensers 20, 20. The vapor was cooled from 46° C. to 37° C. in the condensers 20 and thereby condensed. Cooling water of 30° C. was passed through the heating-medium pipes 26 of the condensers 20.

The column-bottom-liquid-retrieving pipe 32 leading from the distillation column 10 to the reboilers 30 had a pipe diameter of 1,300 mm. The vapor having been boiled from the liquid with the reboilers 30 was returned from the vapor-returning pipes 34 (having a pipe diameter of 1,250 mm) to the distillation column 10. The circulation of the liquid or vapor between the reboilers 30 and the distillation column 10 was carried out by natural circulation. Saturated steam of 0.6 MPaG was supplied to the heating-medium pipes 36 of the reboilers 30. Molecular oxygen gas was supplied at 100 Nm³/h from a lower portion of each reboiler 30.

The operation was continued under the above conditions for 1 month. The inside temperature of the distillation column 10 was stable. For example, the temperature of the 29th plate was in the range of 93 to 97° C. After the end of the operation, the inside of the apparatus was inspected. As a result, no adhesion of the polymer was seen inside any of the distillation column 10, the condensers 20, the reboilers 30, and the pipes.

Comparative Example 2

Based on Example 2, the apparatus specifications and the operational conditions were modified as follows.

The distillation column 10 and the condensers 20 and their disposition structures are common to those of Example 2. However, as to the reboilers 30, only one reboiler of the following specifications was used.

<Reboiler>

Basically, it is common to those of Example 2. The different items of the specifications are as follows.
Tubes: length=4,000 mm, number of tubes=1,788
Shell portion: outer diameter=2,250 mm The treatment ability of the reboiler is equal to the total of the two reboilers of Example 2.

<Purification Operation>

Distillation was carried out under the same operational conditions as of Example 2. A purified material comprising acrylic acid 96.0 weight % and acetic acid 600 weight ppm was obtained as the column bottom liquid. The temperature in the distillation column 10 varied considerably. For example, the temperature of the 29th plate varied in the range of 83 to 96° C. When the operation had been carried out for 12 hours, the pressure drop in the column increased, and therefore the operation was stopped. On inspection of the inside of the distillation column 10, the condensers 20, and the reboiler 30, a polymer was seen in an amount of 130 kg on the trays of the distillation column 10. As to the reboiler 30, unfavorably, ninety-two tubes were clogged up due to the adhesion of the polymer thereto.

Example 3

This example was based on the purification apparatus having the structure shown in FIGS. 3 and 4. However, as to the condensers 20, only one condenser was set. Basically, the specifications common to those of Example 1 were adopted. Only the different items of the specifications are shown below.

<Distillation Column>

The column diameter was changed to 2 m in a structure common to that of Example 1.

<Condenser>

Basically, it is common to those of Example 1. The different items of the specifications are as follows.

Tubes: length=4,000 mm, number of tubes=492, material=SUS 304

Shell portion: outer diameter=1,900 mm

<Reboilers>

Basically, they are common to those of Example 1. The different items of the specifications are as follows.

Tubes: length=4,000 mm, number of tubes=170, material=SUS 304

Shell portion: outer diameter=700 mm

Interposed angle between the two reboilers: θ=180°

<Purification Operation>

An unpurified acrylic ester liquid (containing butyl acrylate 78.0 weight %, butyl alcohol 18.6 weight %, water 2.9 weight %, and phenothiazine 80 weight ppm) was supplied at a flow rate of 8.0 m³/h to the 16th plate of the distillation column 10. Azeotropic distillation was carried out under a column top pressure of 33 kPa at a reflux ratio of 3. A purified material comprising butyl acrylate 99.9 weight % and butyl alcohol 50 weight ppm was obtained as the column bottom liquid.

The vapor-retrieving pipe 22 from the distillation column 10 to the condenser 20 had a pipe diameter of 550 mm. The vapor was cooled from 83° C. to 40° C. in the condenser 20 and thereby condensed. Cooling water of 30° C. was passed through the heating-medium pipe 26 of the condenser 20.

The column-bottom-liquid-retrieving pipe 32 from the distillation column 10 to the reboilers 30 had a pipe diameter of 450 mm. The vapor-returning pipes 34 had a pipe diameter of 550 mm. The circulation of the liquid or vapor between the distillation column 10 and the reboilers 30 was carried out by natural circulation. A portion of the circulating liquid was extracted to the outlet pipe 16. Saturated steam of 0.6 MPaG was supplied to the heating-medium pipe 36 of each reboiler 30. Air was supplied at 4 Nm³/h from a lower portion of each reboiler 30.

The operation was carried out under the above conditions for 1 month. The inside temperature of the distillation column 10 was stable. For example, the temperature of the 35th plate was in the range of 102 to 104° C. After the end of the operation, the inside of the apparatus was inspected. As a result, almost no existence of the polymer was seen inside any of the distillation column 10, the condenser 20, and the reboilers 30.

Comparative Example 3

Based on Example 3, the apparatus specifications and the operational conditions were modified as follows.

The distillation column 10 and the condenser 20 and their disposition structures are common to those of Example 3. However, as to the reboilers 30, only one reboiler of the following specifications was used.

<Reboiler>

Basically, it is common to those of Example 3. The different items of the specifications are as follows.

Tubes: number of tubes=340

Shell portion: outer diameter=950 mm

The treatment ability of the reboiler is equal to the total of the two reboilers of Example 3.

<Purification Operation>

Distillation was carried out under the same operational conditions as of Example 3. A purified material comprising butyl acrylate 99.9 weight % and butyl alcohol 200 weight ppm was obtained as the column bottom liquid.

The temperature in the distillation column 10 varied considerably. For example, the temperature of the 35th plate varied in the range of 99 to 104° C. On inspection of the inside of the apparatus after the operation for 1 month, a polymer was seen in an amount of 6 kg on the trays of the distillation column 10. As to the reboiler 30, unfavorably, five tubes were clogged up due to the adhesion of the polymer thereto.

[Evaluation]

(1) In all the Examples, the temperature in the distillation column was stable without involving the problem of such as adhesion of the polymer or clogging of the inner piping with the polymer. The operation of the purification of the acrylic acid family could be achieved well.

(2) As to the Comparative Examples in which the same treatment abilities as those of the Examples were performed with one reboiler, the purification itself of the acrylic acid family could be carried out. However, unfavorably, in the early stage after the start of the operation, the polymer adhered to the inside of the apparatus, or the inner piping was clogged up with the polymer.

The inside temperature of the distillation column varied much. Therefrom it can be inferred that the channeling occurred to the flow of the liquid or vapor in the distillation column, or that this flow was unstable. As a result, the operation of the purification of the acrylic acid family was also unstable.

(3) From all of Examples 1 and 2 in which the purification of acrylic acid was carried out and Example 3 in which the purification of the acrylic ester was carried out, good results were obtained. Therefrom it can be understood that the present invention is effective to any substance as included in the acrylic acid family.

In Examples 1 and 2, not only is the reboiler set in a number of at least two, but also the condenser is used in a number of at least two. In Example 3, the condenser is set in a number of one. In any case, good performance is displayed. Accordingly, it can be understood that the reboiler needs to be used in a number of at least two, but that, as to the condenser, there is a case where the present invention can be carried out even if the condenser is used in a number of one. As to the case of Example 3 in which the apparatus which is smaller in treatment amount and in size than those used in Examples 1 and 2, it can be inferred that the object could sufficiently be achieved though the condenser was used in a number of one.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for distillation purification of an acrylic acid family encompassing acrylic acid and its esters with an apparatus comprising a distillation column, at least two reboilers, and a condenser, with said at least two reboilers being connected to the column bottom side of the distillation column, with the condenser being connected to the column top side of the distillation column, with the process comprising the steps of:

supplying a liquid containing said acrylic acid family to the distillation column, retrieving a vapor from a column top of said distillation column, retrieving a liquid from a column bottom of said distillation column, selecting an outer diameter of the distillation column to be in a range of 2 to 6 m, selecting a height of the distillation column to be in a range of 2 to 40 m, and selecting a capacity of the distillation column to be in a range of 0.5 to 1,000 m$^3$, supplying the vapor that has been retrieved from the distillation column to the condenser, condensing with the condenser the vapor that has been supplied to the condenser and then refluxing a portion of resultant condensate to the distillation column, retrieving residual condensate from the condenser, supplying the liquid in the distillation column to said at least two reboilers, heat-boiling with said at least two reboilers the liquid that has been supplied to said at least two reboilers and returning said liquid to the distillation column, and setting said at least two reboilers in parallel to the distillation column in order to prevent channeling of the liquid or vapor in the distillation column, thus preventing formation and adhesion of polymer and clogging in the distillation column and in said at least two reboilers.

2. A process for purification of an acrylic acid family according to claim 1, and further comprising the step of disposing at least two condensers in parallel to the distillation column.

3. A process for purification of an acrylic acid family according to claim 1, and further comprising the step of causing equal pressure drops when the liquid passes from the column bottom to said at least two reboilers in order to avoid a problem of liquid, being retrieved from the distillation column, having a bias toward a specific reboiler.

4. A process for purification of an acrylic acid family according to claim 1, and further comprising the step of providing liquid-retrieving pipes, through which said at least two reboilers and the distillation column are connected to each other, to be equal or symmetrical with respect to the distillation column as a center.

5. A process for purification of an acrylic acid family according to claim 1, and further comprising the step of causing equal pressure drops when the liquid passes from said at least two reboilers to the distillation column in order to well disperse gas into the distillation column.

6. A process for purification of an acrylic acid family according to claim 1, and further comprising the step of equipping vapor-returning pipes separately to individual reboilers.

7. A process for purification of an acrylic acid family according to claim 1, and further comprising the step of disposing positions of connections of vapor-returning pipes from said at least two reboilers to the distillation column symmetrically as to the distillation column.

* * * * *